(12) United States Patent
Knevels et al.

(10) Patent No.: US 8,001,856 B2
(45) Date of Patent: Aug. 23, 2011

(54) SAMPLING DEVICE

(75) Inventors: Johan Knevels, Bree (BE); Frank Mingneau, Zonhoven (BE); Guido Neyens, Opoeteren (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 493 days.

(21) Appl. No.: 11/012,473

(22) Filed: Dec. 15, 2004

(65) Prior Publication Data

US 2005/0132823 A1      Jun. 23, 2005

(30) Foreign Application Priority Data

Dec. 19, 2003   (DE) .................................. 103 60 625

(51) Int. Cl.
*G01N 1/12* (2006.01)
(52) U.S. Cl. .................. 73/864.56; 73/864.55
(58) Field of Classification Search ............... 73/864.53, 73/864.55–864.58, 864.59
See application file for complete search history.

(56) References Cited

U.S. PATENT DOCUMENTS

| | | |
|---|---|---|
| 3,321,978 A | 5/1967 | Jackson |
| 3,656,346 A | 4/1972 | Collins |
| 3,656,350 A | 4/1972 | Collins |
| 3,717,034 A | 2/1973 | Dukelow et al. |
| 3,791,219 A | 2/1974 | Falk |
| 3,798,974 A | 3/1974 | Boron |
| 3,820,380 A | 6/1974 | Miller et al. |
| 3,877,309 A | 4/1975 | Hance |
| 4,002,072 A | 1/1977 | Collins |
| 4,007,641 A * | 2/1977 | Kelsey ...................... 73/864.54 |
| 4,059,996 A | 11/1977 | Cure |
| 4,089,223 A | 5/1978 | Collins |
| 4,179,931 A | 12/1979 | Moriya |
| 4,291,585 A | 9/1981 | Kolb et al. |
| 4,338,841 A | 7/1982 | Collins |
| 4,338,842 A | 7/1982 | Collins |
| 4,361,053 A | 11/1982 | Jones et al. |
| 4,503,716 A | 3/1985 | Wuensch |
| 4,515,485 A | 5/1985 | Cassidy et al. |
| 4,932,271 A | 6/1990 | Haughton |
| 4,941,364 A | 7/1990 | Haughton |

(Continued)

FOREIGN PATENT DOCUMENTS

DE        7405180 U        6/1974

(Continued)

OTHER PUBLICATIONS

Office Action issued on Jun. 21, 2004 in U.S. Appl. No. 10/340,416.

(Continued)

*Primary Examiner* — Robert R Raevis
(74) *Attorney, Agent, or Firm* — Panitch Schwarze Belisario & Nadel LLP

(57) ABSTRACT

A sampling device for molten metals is provided having a carrier tube and a sample chamber fixed in the carrier tube, with an inlet piece for the molten metal flowing into the sample chamber. In the inlet piece there is arranged an inlet tube, which has an outlet into the sample chamber and an inlet opening at its other end. The outlet as well as the inlet opening of the inlet tube has a reduced cross section relative to the central part of the inlet tube. The inlet tube is formed of quartz glass, and the wall of the inlet tube is crimped toward the axis of the inlet tube at its two ends.

4 Claims, 2 Drawing Sheets

U.S. PATENT DOCUMENTS

| | | | |
|---|---|---|---|
| 5,057,149 | A | 10/1991 | Conti et al. |
| 5,151,243 | A | 9/1992 | Auer et al. |
| 5,537,881 | A | 7/1996 | White |
| 5,948,350 | A | 9/1999 | Falk |
| 5,979,253 | A | 11/1999 | Knevels et al. |
| 6,155,122 | A | 12/2000 | Junker et al. |
| 6,370,973 | B1 | 4/2002 | Wunsch et al. |
| 6,581,482 | B2 | 6/2003 | Cappa et al. |
| 6,811,742 | B2 | 11/2004 | Knevels |
| 6,883,392 | B2 | 4/2005 | Knevels et al. |
| 2001/0020397 | A1 | 9/2001 | Cappa et al. |
| 2003/0062661 | A1 | 4/2003 | Knevels |
| 2010/0122590 | A1 | 5/2010 | Knevels |

FOREIGN PATENT DOCUMENTS

| | | |
|---|---|---|
| DE | 26 46 539 A1 | 10/1977 |
| DE | 2840745 B2 | 3/1980 |
| DE | 3402818 A1 | 8/1985 |
| DE | 27 14636 C2 | 11/1986 |
| DE | 89 10 869 U1 | 12/1989 |
| DE | 40 09 167 C2 | 1/1992 |
| DE | 19752743 A1 | 6/1999 |
| DE | 10049253 A1 | 9/2001 |
| EP | 0 447 613 A2 | 10/1990 |
| EP | 0 436 063 B1 | 7/1991 |
| EP | 1126036 A1 | 8/2001 |
| FR | 2026247 A1 | 9/1970 |
| FR | 2171627 A5 | 9/1973 |
| GB | 1235800 A | 6/1971 |
| GB | 2335738 A | 9/1999 |
| JP | 24187/1972 | 11/1972 |
| JP | 083217/85 | 5/1985 |
| JP | 61077761 A | 4/1986 |
| JP | 61271452 A | 12/1986 |
| JP | 05273197 A | 10/1993 |
| JP | 06265539 A | 9/1994 |
| JP | 07306196 A | 11/1995 |
| JP | 11304669 A | 11/1999 |
| SU | 601595 A1 | 4/1978 |
| SU | 1411612 A1 | 7/1988 |
| WO | 0073765 A1 | 12/2000 |

OTHER PUBLICATIONS

European Search Report issued on Jun. 25, 2004 in European Application No. EP 02 02 7794.

Office Action issued ion Mar. 11, 2010 in German Application No. 10 2008 057 797.9-52.

Office Action issued on Feb. 1, 2002 in German Application No. 101 48 112.8-52.

Office Action issued on Apr. 6, 2004 in U.S. Appl. No. 10/256,898.

Office Action issued on Oct. 6, 2003 in U.S. Appl. No. 10/256,898.

Office Action issued on Aug. 22, 2002 in U.S. Appl. No. 09/788,224.

Office Action issued on Jan. 16, 2001 in German Application No. 100 49 253.3-52 (copy submitted with Information Disclosure Statement filed Feb. 16, 2001 in U.S. Appl. No. 09/788,224).

Office Action issued on Jun. 22, 2001 in European Application No. EP 01 10 3404 (copy submitted with Information Disclosure Statement filed Aug. 14, 2001 in U.S. Appl. No. 09/788,224).

Office Action issued on May 14, 2002 in German Application No. DE 102 01 0234.4-52 (with partial English translation).

* cited by examiner

SAMPLING DEVICE

BACKGROUND OF THE INVENTION

The invention relates to a sampling device for molten metals, especially for iron or steel melts, having a carrier tube and a sample chamber fixed in the carrier tube with an inlet piece for the molten metal flowing into the sample chamber.

Such sampling devices are known from Japanese Utility Model Application No. 24340/1971 (Public Disclosure No. 24187/1972). Here, a sampling device is described having a thick-walled inlet piece, in whose wall a pre-chamber is incorporated. In Japanese Utility Model Application Public Disclosure No. 83217/1985 a sampling device is described having a sample chamber, which forms a structural unit with the material of a pre-chamber. In German Patent DE 2714636 C2 a sample chamber is described having an inlet tube, whose cross section is reduced multiple times in the central part of the tube by crimping on one side.

Further sampling devices are known from Japanese Published Patent Application (Kokai) JP 07306196A. The sampling device described here has an inlet tube that is tapered on its inlet end into the sample chamber. At this tapered section, the sample can be separated from the inlet end.

BRIEF SUMMARY OF THE INVENTION

The invention is based on the object of improving the known sampling devices in order to guarantee reliable sampling.

The object is achieved by a sampling device for molten metals having a carrier and a sample chamber fixed in the carrier tube, having an inlet piece for the molten metal flowing into the sample chamber, with the inlet piece expediently formed on the sample chamber, having an inlet tube arranged in the inlet piece, and the inlet tube having an outlet into the sample chamber and an inlet opening on its other end. The outlet as well as the inlet opening of the inlet tube has a reduced cross section relative to the central part of the inlet tube. The inlet tube is formed of quartz glass, and the wall of the inlet tube is crimped toward the axis of the inlet tube at its two ends.

The in-flowing molten metal is thereby slowed so that destruction of the sample chamber during the sampling is prevented to the greatest extent. By the practical double-walled inlet, the heat transfer at this position is minimal, so that molten metal does not solidify on the wall of the inlet tube. Thus, the arrangement of the quartz tube, which exhibits a relatively low heat expansion, in an inlet piece formed on the sample chamber is therefore also advantageous, because the separation of the sample from the metal located in the inlet tube is thereby reliably guaranteed.

A deoxidation means for the in-flowing molten metal can be arranged in the sample chamber. The sample chamber can be formed from two, preferably metallic, half shells. By the arrangement according to the invention, a melting off of the sample chamber or an adhesion of the half shells is prevented. The inlet tube forms a sort of pre-chamber, which is used as a mixing chamber. In addition, it can be expedient if the inlet tube has a cross-sectional change in at least one position between the outlet and the inlet opening, compared with the adjacent regions of the inlet tube, because this condition additionally favors the separation of the solidified sample from the solidified material inside the inlet tube.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
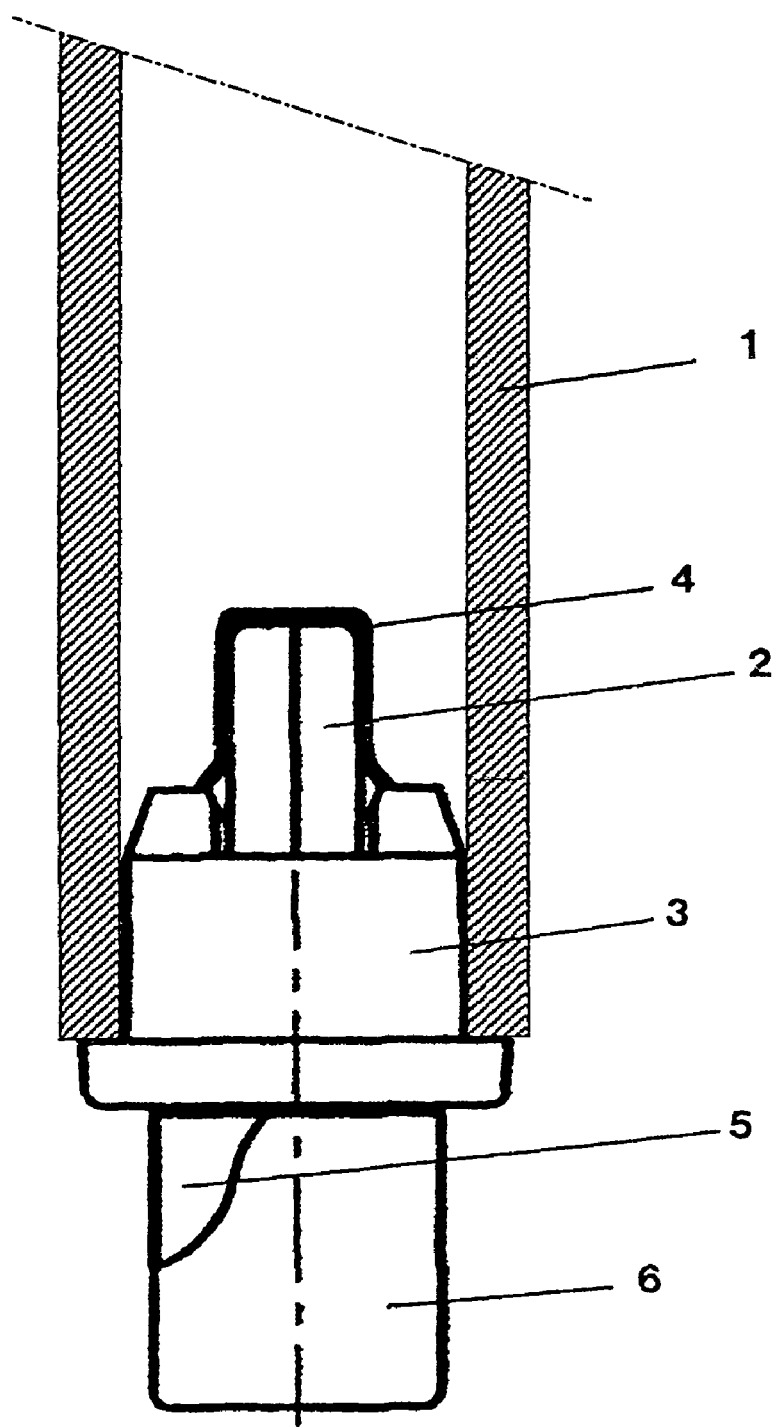
FIG. 1 is a side view, partially in section, of a sampling device according to the invention.

A sample chamber 2 is arranged within or on a carrier tube 1 (FIG. 1). The sample chamber 2 is formed by walls 7 in a known and conventional manner from two half shells made of metal (steel), wherein the two half shells have a nearly circular, larger cross section, while the cross section perpendicular thereto is approximately rectangular, in order to realize on the sample two flat analysis surfaces that are as large as possible. The walls 7 of the sample chamber 2 are fixed in the carrier tube by means of a sand body 3 (molding sand), and the two half shells are held together with a clamp 4. The immersion end of the sampling device is closed with a metal cap 5, which is covered with another cap 6 made of cardboard.

Figure 2:
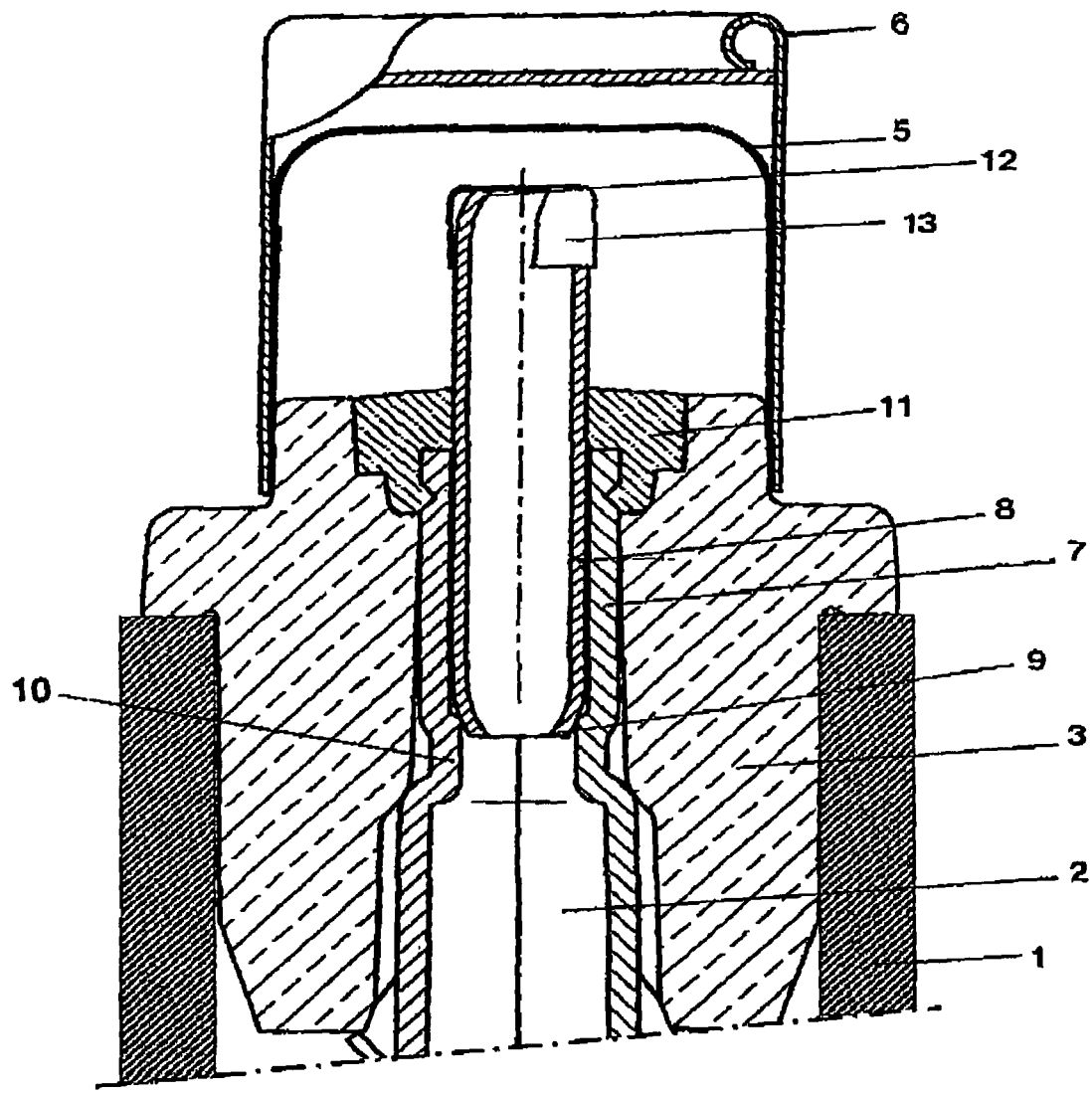
FIG. 2 is an enlarged cross sectional side view of the sampling device of FIG. 1 showing the inlet tube and the outlet into the sample chamber.

An inlet piece formed of the upper portion of the walls 7 in FIG. 2 and made of the same material attaches directly to the sample chamber 2, in which an inlet tube 8 made of quartz glass is arranged (FIG. 2). In this example, the inlet tube 8 is held at its outlet 9 facing the sample chamber 2 by a narrowed section 10 of the walls 7. The inlet tube 8 has at its outlet 9 a reduced cross section, which is produced by deforming (crimping) the wall of the inlet tube 8 in the direction of its axis. The reduction of the radius of the outlet 9 relative to the inner radius of the inlet tube 8 is dependent on the wall thickness of the inlet tube 8. The distance from the outlet 9 to the inner wall of the sample chamber 2 equals approximately 5 mm. The walls 7 of the inlet piece and the inlet tube 8 are fixed in the sand body 3 by means of cement 11. At the inlet opening 12, the second end of the inlet tube 8 is reduced in its cross section in the same way as the outlet 9. The inlet opening 12 is covered with a steel cap 13, which serves for protecting the inlet tube 8 and for slowing the in-flow of the molten metal. The caps 5; 6; 13 dissolve upon immersion of the device in the molten metal or in the molten metals, so that the liquid metal can flow into the sample chamber 2 through the inlet tube 8, in which a mixing and homogenizing process takes place.

The size of the cross-sectional reduction of the outlet 9 can be adapted to the appropriate application. The lower the overheating of the melt, the smaller the diameter of the outlet 9 should be relative to the inner diameter of the inlet tube 8. For example, for sampling from the converter with an over-heating of approximately 60° C., a functional sampling device is constructed with a reduction of the inner diameter of the tube from 8 mm to 5.5 mm for an outer tube diameter of 10 mm.

With the use of inlet tubes 8 having a wall thickness of at least 2 mm, it can be useful to provide a further change in diameter of the inlet tube 8. However, smaller wall thicknesses of the inlet tube 8 are generally more advantageous.

After the molten metal flows into the sample chamber 2, the melt begins to solidify. At the reduced cross section of the outlet 9 of the inlet tube 8, the solidified molten metal cracks, so that the sample can be removed from the sampling device without the solidified metal located in the inlet tube 8.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A sampling device for molten metals comprising a carrier tube and walls fixed in the carrier tube, the walls forming a sample chamber and an inlet piece for the molten metal flowing into the sample chamber, the sample chamber being made of metal and an inlet tube arranged in the inlet piece, the inlet tube having an outlet facing the sample chamber and an inlet opening on its other end, the outlet and the inlet opening of the inlet tube having a reduced cross section relative to a central part of the inlet tube, wherein the inlet tube comprises quartz glass, a wall of the inlet tube is crimped toward a longitudinal axis of the inlet tube at its two ends, and a diameter at the reduced cross section of the outlet is of a size such that the molten metal cracks at the reduced cross section of the outlet as the molten metal begins to solidify.

2. The sampling device according to claim 1, wherein the inlet tube has a change in cross section, compared with adjacent regions of the inlet tube, in at least one position between the outlet and the inlet opening.

3. The sampling device according to claim 1, wherein the walls comprise two half shells forming the sample chamber.

4. The sampling device according to claim 1, wherein the ends of the quartz tube are crimped at an angle of approximately 45°.

* * * * *